United States Patent
Lim et al.

(10) Patent No.: US 11,198,666 B2
(45) Date of Patent: Dec. 14, 2021

(54) METHOD FOR PREPARING (METH)ACRYLIC ACID ESTER BASED COMPOUND

(71) Applicant: LG Chem, Ltd., Seoul (KR)

(72) Inventors: Won Taeck Lim, Daejeon (KR); Ji Eun Kim, Daejeon (KR); Wonmun Choi, Daejeon (KR); Yongjin Kim, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 17/053,588

(22) PCT Filed: Feb. 13, 2020

(86) PCT No.: PCT/KR2020/002019
§ 371 (c)(1),
(2) Date: Nov. 6, 2020

(87) PCT Pub. No.: WO2020/226271
PCT Pub. Date: Nov. 12, 2020

(65) Prior Publication Data
US 2021/0130279 A1    May 6, 2021

(30) Foreign Application Priority Data

May 9, 2019   (KR) .................. 10-2019-0054493
Feb. 12, 2020  (KR) .................. 10-2020-0017053

(51) Int. Cl.
*C07C 67/08*   (2006.01)
*C07C 67/58*   (2006.01)
*C07C 69/54*   (2006.01)

(52) U.S. Cl.
CPC .............. *C07C 67/08* (2013.01); *C07C 67/58* (2013.01); *C07C 69/54* (2013.01)

(58) Field of Classification Search
CPC .................... C07C 67/08; C07C 67/58
See application file for complete search history.

(56) References Cited

U.S. PATENT DOCUMENTS 8,859,804 B2 * 10/2014 Ansai ................ C07C 67/08
                                                         560/220
2002/0143120 A1  10/2002  Yurugi et al.
2011/0190464 A1   8/2011  Dubois et al.
2011/0301379 A1  12/2011  Ansai et al.
2012/0165572 A1   6/2012  Iwai et al.
2017/0050912 A1   2/2017  Matsuo et al.
2018/0050975 A1   2/2018  Takahata et al.

FOREIGN PATENT DOCUMENTS

| JP | 2001106652 A | 4/2001 |
| JP | 2012144513 A | 8/2012 |
| JP | 2014091725 A | 5/2014 |
| JP | 2014205668 A | 10/2014 |
| KR | 20020031318 A | 5/2002 |
| KR | 100543821 B1 | 1/2006 |
| KR | 20110112870 A | 10/2011 |
| KR | 20170128338 A | 11/2017 |
| KR | 101898362 B1 | 9/2018 |

OTHER PUBLICATIONS

International Search Report for Application No. PCT/KR2020/002019 dated May 29, 2020, 3 pages.

* cited by examiner

*Primary Examiner* — Yate' K Cutliff
(74) *Attorney, Agent, or Firm* — Lerner, David, Littenberg, Krumholz & Mentlik, LLP

(57) ABSTRACT

The invention relates to a method for preparing a (meth)acrylic acid ester-based compound, and according to the preparation method, a (meth)acrylic acid ester-based compound can be prepared with high purity and high yield, by easily introducing an acrylic structure into alcohol using a diamine-based compound and acid anhydride.

15 Claims, No Drawings

METHOD FOR PREPARING (METH)ACRYLIC ACID ESTER BASED COMPOUND

CROSS-REFERENCE TO RELATED APPLICATIONS

The present application is a national phase entry under 35 U.S.C. § 371 of International Application No. PCT/KR2020/002019, filed on Feb. 13, 2020, which claims priority to Korean Patent Application No. 10-2019-0054493 filed on May 9, 2019 and Korean Patent Application No. 10-2020-0017053 filed on Feb. 12, 2020, the disclosures of which are herein incorporated by reference in their entirety.

TECHNICAL FIELD

The invention relates to a method for preparing a (meth)acrylic acid ester-based compound, and according to the preparation method, a (meth)acrylic acid ester-based compound, particularly a (meth)acrylic acid ester-based compound with high steric hindrance can be prepared with high purity and high yield, by easily introducing an acrylic structure into alcohol using a diamine-based compound and acid anhydride.

BACKGROUND ART

An acrylic structure is a representative functional structure of monomers for polymerization. Due to the acrylic structure, polymerized polymer may be used for various applications such as an adhesive, superabsorbent polymer (SAP), and the like.

Thus, methods for introducing an acrylic structure into monomers have been continuously studied, but there are many limitations to the preparation of structurally complicated acrylic acid ester monomers.

In general, esterification hardly occurs in a highly structurally hindered structure, i.e., a highly sterically hindered structure. Thus, when preparing acrylic acid ester monomers having high steric hindrance, a method of using acryloyl chloride or acrylic anhydride as raw materials and reacting them with alcohol is mainly used.

However, in case acryloyl chloride is used as raw material, it is difficult for an operator to handle, and in case acrylic anhydride is used, due to the high reaction temperature of 110° C. or more, polymerization reactions between the produced acrylic acid esters are likely to be progressed. In addition, both materials are expensive, and raise environmental and safety problems, thus rendering mass production difficult.

And, since high sterically hindered alcohol such as tertiary alcohol has low reactivity, when reacting with acryloyl chloride or acrylic anhydride, base such as triethylamine or 4-dimethylamino pyridine (DMAP) is used, and in this case, acrylic acid ester conversion and yield are low.

Thus, the inventors confirmed that in case a diamine-based compound and acid anhydride are used when synthesizing acrylic acid ester, an acrylic structure can be easily introduced into alcohol, particularly sterically hindered alcohol, and thus, a (meth)acrylic acid ester-based compound can be prepared with high purity and high yield, and completed the invention.

DETAILED DESCRIPTION OF THE PRESENT DISCLOSURE

Technical Problem

It is an object of the invention to provide a preparation method capable of preparing a (meth)acrylic acid ester-based compound, particularly a (meth)acrylic acid ester-based compound having high steric hindrance with high purity and high yield, by easily introducing an acrylic structure into alcohol using a diamine-based compound and acid anhydride.

Technical Solution

According to one embodiment of the invention, there is provided a method for preparing a (meth)acrylic acid ester-based compound of the following Chemical Formula 1, comprising the step of reacting a an alcohol-based compound of the following Chemical Formula 2 and a (meth)acrylic acid-based compound of the following Chemical Formula 3, in the presence of a diamine-based compound of the following Chemical Formula 4 and acid anhydride of the following Chemical Formula 5:

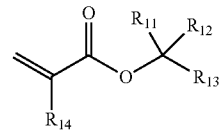

[Chemical Formula 1]

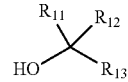

[Chemical Formula 2]

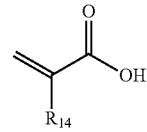

[Chemical Formula 3]

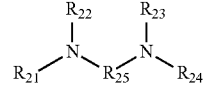

[Chemical Formula 4]

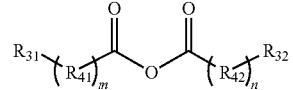

[Chemical Formula 5]

in the Chemical Formulae 1 to 5, $R_{11}$ to $R_{13}$ are each independently, hydrogen, substituted or unsubstituted $C_{1-20}$ alkyl, or substituted or unsubstituted $C_{3-20}$ cycloalkyl, or two neighboring functional groups are linked to form an alicyclic structure, $R_{14}$ is hydrogen or methyl, $R_{21}$ to $R_{24}$ are each independently, hydrogen, or substituted or unsubstituted $C_{1-10}$ alkyl, $R_{25}$ is substituted or unsubstituted $C_{1-10}$ alkylene, $R_{31}$ and $R_{32}$ are each independently, hydrogen or methyl, $R_{41}$ and $R_{42}$ are each independently, substituted or unsubstituted $C_{1-10}$ alkylene, m and n are each independently, an integer of 0 or 1, provided that when both m and n are 0, each of $R_{31}$ and $R_{32}$ is methyl.

Hereinafter, the invention will be explained in detail.

As used herein, the term "substituted or unsubstituted" means unsubstituted or substituted with one or more substituents selected from the group consisting of deuterium; a halogen group; a nitrile group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing one or more selected from N, O and S atoms, or unsubstituted or substituted with a substituent in which two or more of the above illustrated substituents are connected. For example, "a substituent in which two or more substituents are connected" may be a biphenyl group. Namely, a biphenyl group may be an aryl group, or it may be interpreted as a substituent in which two phenyl groups are connected.

As used herein, an "alkyl group" may be a linear or branched chain, and the carbon number is not specifically limited, but may be 1 to 20, more specifically 1 to 12 or 1 to 6. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, or 5-methylhexyl, and the like, but are not limited thereto.

As used herein, a "cycloalkyl group" is a saturated hydrocarbon based functional group having a ring structure (or an alicyclic alkyl group), and it may have a monocylic or polycyclic structure. The carbon number of the cycloalkyl group is not specifically limited, but may be 3 to 20, more specifically 3 to 12 or 3 to 6. Specific examples thereof may include cyclopropyl, cyclobutyl, cyclopentyl, cyclohexyl, or adamantyl, and the like, but are not limited thereto.

As used herein, to "alkylene", explanations about the above explained alkyl group may be applied, except that it is a divalent group. Specific examples thereof may include methylene, ethylene, propylene, or butylenes, and the like, but are not limited thereto.

The method for preparing a (meth)acrylic acid ester-based compound of the Chemical Formula 1 according to one embodiment comprises a step of reacting a an alcohol-based compound of the Chemical Formula 2 and a (meth)acrylic acid-based compound of the Chemical Formula 3, in the presence of a diamine-based compound of the Chemical Formula 4 and acid anhydride of the Chemical Formula 5.

If a reaction is conducted under the above conditions, the diamine-based compound of the Chemical Formula 4 reacts with the above reactants, and specifically, it reacts first with the (meth)acrylic acid-based compound to form an acryl-diaminoalkane cation. Subsequently, the acid anhydride of the Chemical Formula 5 reacts with acryl of the acryl-diaminoalkane cation to form acryl-alkyl mixed anhydride, which is a key material for preparing acrylic acid ester, and the formed mixed anhydride reacts with the acryl-diaminoalkane cation again to lower activation energy, thereby promoting the esterification reaction of the alcohol-based compound of the Chemical Formula 2 having high steric hindrance and (meth)acrylic acid-based compound of the Chemical Formula 3.

Thus, in the preparation method according to one embodiment, if the acid anhydride of the Chemical Formula 5 is used alone without the diamine-based compound of the Chemical Formula 4, acryl-diaminoalkane cation for promoting the esterification reaction may not be formed, and thus, reaction efficiency may be remarkably lowered. And, if acid anhydrides other than the acid anhydride of the Chemical Formula 5 are used, a separate high cost process is required for the formation of mixed anhydride, but if the acid anhydride of the Chemical Formula 5 is used, mixed anhydride is formed in-situ, and thereafter, an esterification reaction for the synthesis of acrylic acid ester may be progressed selectively and in stages, and thus, acrylic acid ester, particularly acrylic acid ester with high steric hindrance can be prepared with high purity and high yield.

In the above preparation method, the reactant alcohol-based compound of the Chemical Formula 2 may be primary alcohol of the Chemical Formula 2 wherein all of $R_{11}$ to $R_{13}$ are hydrogen atoms, or two of $R_{11}$ to $R_{13}$ are hydrogen atoms, and the others are substituted or unsubstituted $C_{1-20}$ alkyl, or substituted or unsubstituted $C_{3-20}$ cycloalkyl; or secondary or tertiary alcohol of the Chemical Formula 2 having high steric hindrance wherein $R_{11}$ to $R_{13}$ are each independently, hydrogen, substituted or unsubstituted $C_{1-20}$ alkyl, or substituted or unsubstituted $C_{3-20}$ cycloalkyl, or two neighboring functional groups are linked to form an alicyclic structure, provided that two or more of $R_{11}$ to $R_{13}$ are not simultaneously hydrogen.

If the alcohol-based compound is secondary or tertiary alcohol, it may be a compound of the Chemical Formula 2 wherein $R_{11}$ to $R_{13}$ are each independently, hydrogen, substituted or unsubstituted $C_{1-12}$ alkyl, or substituted or unsubstituted $C_{3-12}$ cycloalkyl, or two neighboring functional groups are linked to form a $C_{6-12}$ alicyclic, provided that two or three of $R_{11}$ to $R_{13}$ are not simultaneously hydrogen. As such, even if the alcohol-based compound is secondary or tertiary alcohol having high steric hindrance, a (meth)acrylic acid ester-based compound with high steric hindrance can be prepared with high purity and high yield by the esterification reaction using the diamine-based compound of the Chemical Formula 4 and acid anhydride of the Chemical Formula 5.

And, in the Chemical Formula 1, if $R_{11}$ to $R_{13}$ are substituted, they may be substituted with one or more of $C_{1-6}$ linear or branched alkyl, or $C_{3-6}$ cycloalkyl, more specifically, $C_{1-4}$ linear or branched alkyl, such as methyl, ethyl, isopropyl, and t-butyl.

More specifically, the alcohol-based compound may be a compound of the Chemical Formula 2, wherein $R_{11}$ to $R_{13}$ are each independently, $C_{1-6}$ linear or branched alkyl, such as methyl, ethyl, propyl, isopropyl, t-butyl, and the like; or $C_{3-6}$ cycloalkyl, such as cyclopropyl, cyclobutyl, cyclohexyl, and the like, or one of $R_{11}$ to $R_{13}$, for example $R_{11}$ is hydrogen, and the other two functional groups, for example $R_{12}$ and $R_{13}$ are linked with each other to form a $C_{6-10}$ alicyclic structure, unsubstituted or substituted with $C_{1-6}$ linear or branched alkyl, such as cyclohexyl, cycloheptyl, methylcyclohexyl, 2-isopropyl-5-methylcyclohexyl, and the like.

Specific examples of the alcohol-based compound may include t-BuOH or menthol, and the like, but not limited thereto.

And, the (meth)acrylic acid-based compound of the Chemical Formula 3 that reacts with the alcohol-based compound is a compound providing an acrylic structure for the finally prepared acrylic acid ester-based compound, and specifically, it may be acrylic acid of the Chemical Formula 3 wherein $R_{14}$ is hydrogen, or methacrylic acid of the Chemical Formula 3 wherein $R_{14}$ is methyl.

The (meth)acrylic acid-based compound may be used at a mole ratio of 1 to 3, more specifically 1.5 to 2.3, based on 1 mole of the alcohol-based compound. If the amount of the (meth)acrylic acid-based compound based on 1 mole of the alcohol-based compound is less than 1 mole, the content of non-reacted alcohol-based compounds may increase, and thus, there is a concern about the generation of by-products. And, if the amount of the (meth)acrylic acid-based compound is greater than 3 moles, due to the use of an excessive amount of the (meth)acrylic acid-based compound, extraction efficiency and purity may decrease.

Meanwhile, the reaction of the alcohol-based compound and (meth)acrylic acid-based compound is conducted in the presence of a diamine-based compound of the Chemical Formula 4 and acid anhydride of the Chemical Formula 5.

The diamine-based compound is a compound containing two amino groups, and when preparing an acrylic acid ester-based compound, it reacts first with the reactants to form acryl-diaminoalkane cation, as explained above. Thereby, the activation energy of the reaction is lowered, and thus, the reaction may occur at lower temperature, compared to the conventional acrylic acid ester-based compound preparation reaction, and polymerization reactions between acrylic acid ester-based compounds may be prevented during the reaction.

Previously, when preparing a (meth)acrylic acid ester-based compound through the reaction of an alcohol-based compound and acrylic acid or anhydride thereof, triethylamine (TEA) was used as a catalyst. However, in this case, the rate of by-product acetic acid ester increased. However, since the diamine-based compound is used herein, the diamine-based compound reacts with reactants to form acryl-diaminoalkane cation, and then, a (meth)acrylic acid ester-based compound is formed through the subsequent reaction, there is no concern about the generation of by-products due to acetylation, and an acrylic acid ester-based compound can be prepared with high purity and high yield.

And, compared to the conventional preparation method using an esterification catalyst, the amount of reactants used to obtain the same amount of product may be decreased, and a dropwise addition process is not required, and thus, the preparation process may be simplified and process time and process cost may be reduced.

The diamine-based compound may be specifically, a compound of the Chemical Formula 4 wherein $R_{21}$ to $R_{24}$ are each independently, hydrogen, or substituted or unsubstituted $C_{1-10}$ alkyl, $R_{25}$ is substituted or unsubstituted $C_{1-10}$ alkylene, and the $R_{21}$ to $R_{24}$ may be substituted with $C_{1-6}$ linear or branched alkyl, or $C_{3-6}$ cycloalkyl, more specifically, substituted with one or more of $C_{1-4}$ linear or branched alkyl, such as methyl, ethyl, isopropyl, t-butyl.

More specifically, the diamine-based compound may be a compound of the Chemical Formula 4 wherein $R_{21}$ to $R_{24}$ are each independently, hydrogen; or $C_{1-6}$ linear or branched alkyl such as methyl, ethyl, propyl, isopropyl, t-butyl, and the like, $R_{25}$ is $C_{1-6}$ alkylene such as methylene, ethylene, propylene, and the like, and more specifically, a compound of the Chemical Formula 4 wherein $R_{21}$ and $R_{22}$ are methyl, $R_{23}$ and $R_{24}$ are each independently hydrogen or methyl, and $R_{21}$ is methylene or ethylene.

Specific examples of the diamine-based compound may include N,N,N',N'-tetramethylethylenediamine (TMEDA), N,N-dimethylethylene-1,2-diamine, N,N,N',N'-tetramethylpropylenediamine, or N,N,N',N'-tetramethylbutylenediamine, and the like, and among them, TMEDA may be more preferable, considering the purity and yield improvement effect when preparing a (meth)acrylic acid ester-based compound.

The diamine-based compound may be used at a mole ratio of 0.5 to 1.5, or 0.8 to 1.2, based on 1 mole of the alcohol-based compound. If the mole ratio of the diamine-based compound to the alcohol-based compound is less than 0.5, acryl-diaminoalkane cation may not be sufficiently formed, and thus, conversion may be lowered, and if the mole ratio is greater than 1.5, purity and extraction efficiency may be lowered.

And, the acid anhydride of the Chemical Formula 5 reacts with the acryl-diaminoalkane cation that is formed by the reaction of the reactants for the preparation of an acrylic acid ester-based compound and the diamine-based compound, thus forming acryl-alkyl mixed anhydride, which is key material for the preparation of acrylic acid ester, and the formed mixed anhydride reacts with acryl-diaminoalkane cation again to promote the esterification reaction between the alcohol-based compound having high steric hindrance and the (meth)acrylic acid-based compound.

Previously, when preparing (meth)acrylic acid ester having high steric hindrance, acrylic anhydride was mainly used to promote an esterification reaction, but since the reaction temperature of acrylic anhydride is high (110° C. or more), polymerization between the produced acrylic acid esters was generated. In this regard, by using the acid anhydride having the structure of the Chemical Formula 5, a reaction may occur at lower temperature than before, and thus, polymerization between acrylic acid ester-based compounds may be prevented.

The acid anhydride may be specifically, alkanoic anhydride of the Chemical Formula 5 wherein $R_{31}$ and $R_{32}$ are each independently, hydrogen or methyl, $R_{41}$ and $R_{42}$ are each independently, substituted or unsubstituted $C_{1-6}$ or $C_{1-4}$ alkylene, and m and n are each independently, an integer of 0 or 1, provided that when both m and n are 0, each of $R_{31}$ and $R_{32}$ is methyl.

And, in the Chemical Formula 5, each of $R_{41}$ and $R_{42}$ may be independently substituted, wherein the substituent may be appropriately selected considering the structure of a (meth)acrylic acid ester-based compound to be prepared. Specifically, each of $R_{41}$ and $R_{42}$ may be independently substituted with $C_{1-6}$ alkyl, more specifically $C_{1-4}$ alkyl. If $R_{41}$ and $R_{42}$ are substituted with halogen, or hetero hydrocarbon containing a hetero atom, it may be difficult to prepare a (meth)acrylic acid ester-based compound. For example, in the case of halogen-containing substituent such as trichloro, trifluoro, and the like, acetyl-ester such as trichloroacetyl-ester may be formed instead of acryl-ester, and it may be difficult to apply.

And, specific examples of the acid anhydride may include acetic anhydride, propanoic anhydride, acetic propanoic anhydride, butyric anhydride, isobutyric anhydride, isovaleric anhydride, trimethylacetic anhydride, and the like, and among them, acetic anhydride may be more preferable because yield and conversion of a (meth)acrylic acid ester-based compound may be further improved, and preparation cost may be reduced through recovery and reuse.

The acid anhydride may be used at a mole ratio of 1 to 1.5, or 1.2 to 1.3, based on 1 mole of the alcohol-based compound. If the mole ratio of the acid anhydride to the alcohol-based compound is less than 1, a conversion may be lowered, and if the mole ratio is greater than 1.5, alkyl ester formation side reactions may be generated.

In the preparation method according to one embodiment, the reaction of the alcohol-based compound and the (meth)acrylic acid-based compound may be conducted under a non-solvent condition. Thus, the preparation process may be simplified, and there is no concern about environmental and safety problems due to the use of solvents.

And, the reaction of the alcohol-based compound and the (meth)acrylic acid-based compound may be conducted at 50° C. or more and 80° C. or less, or 60° C. or more and 70° C. or less. If the reaction temperature is less than 50° C., conversion may be lowered, and if it is greater than 80° C., the probability of polymerization between acrylic acid esters during the reaction may increase, and thus, yield may be lowered.

Specifically, the reaction of the alcohol-based compound and the (meth)acrylic acid-based compound may be conducted through primary mixing of the alcohol-based compound and the (meth)acrylic acid-based compound, secondary mixing of the resultant primary mixture with the diamine-based compound, and tertiary mixing of the resultant secondary mixture with the acid anhydride.

More specifically, the reaction of the alcohol-based compound and the (meth)acrylic acid-based compound may be conducted by step 1 in which the alcohol-based compound and the (meth)acrylic acid-based compound are mixed; step 2 in which the mixture obtained as the result of the step 1 is mixed with the diamine-based compound and reacted; and step 3 in which the reactant obtained as the result of the step 2 is mixed with the acid anhydride and reacted, wherein the reactant obtained as the result of the step 2 comprises acryl-diaminoalkane cation produced by the reaction of the diamine-based compound and the (meth)acrylic acid-based compound.

The primary to tertiary mixing processes may be conducted by a common mixing method.

However, since the reaction is conducted under a non-solvent condition, a large quantity of heat may be generated during the primary and secondary mixing. Thus, it may be preferable that the primary mixing and the secondary mixing are conducted at 0° C. or less, more specifically 0 to −15° C., and for this, the primary mixing and the secondary mixing may be conducted in an ice bath.

And, after completing the secondary mixing, the tertiary mixing may be conducted under the above described reaction temperature condition. Thus, after completing the secondary mixing, the tertiary mixing may be conducted in an oil bath of 50 to 80° C.

Through the above processes, (meth)acrylic acid ester represented by the Chemical Formula 1 is prepared.

Wherein, in order to further improve the purity of the prepared (meth)acrylic acid ester-based compound, the resulting reactant may be optionally subjected to an extraction purification process using hexane, and the like, and thus, the preparation method according to one embodiment of the invention may further comprise an extraction purification process after the reaction.

The extraction purification process may be conducted by a common method, and the detailed explanations thereof are omitted.

As explained, by the preparation method according to one embodiment of the invention, a (meth)acrylic acid ester-based compound can be prepared with high purity and high yield, even by a single synthesis reaction.

Specifically, by the above preparation method, a (meth)acrylic acid ester-based compound can be prepared with high purity of 90% or more, or 95% or more, and with high yield of 60% or more, or 65% or more, or 80%.

The yield of (meth)acrylic acid ester can be calculated according to the following Mathematical Formula 1.

Yield (%)=[(mole number of (meth)acrylic acid ester produced after extraction)/(mole number of alcohol-based compound of Chemical Formula 2 used)]*100     [Mathematical Formula 1]

And, the preparation method according to one embodiment may lower reaction activation energy using the diamine-based compound of the Chemical Formula 4 and the acid anhydride of the Chemical Formula 5, thereby easily introducing an acrylic structure even in highly sterically hindered alcohol, and thus, it may be useful for the preparation of a (meth)acrylic acid ester-based compound having high steric hindrance, specifically, a (meth)acrylic acid ester-based compound of the Chemical Formula 1, wherein $R_{11}$ to $R_{13}$ are each independently, hydrogen, substituted or unsubstituted $C_{1-20}$ alkyl, or substituted or unsubstituted $C_{3-20}$ cycloalkyl, or two neighboring functional groups are linked to form an alicyclic structure, provided that two or more of $R_{11}$ to $R_{13}$ are not simultaneously hydrogen.

And, the (meth)acrylic acid ester prepared by the above preparation method, although not limited hereto, may be used for an adhesive, superabsorbent polymer, or a crosslinking agent, and the like.

Advantageous Effects

According to the preparation method, a (meth)acrylic acid ester-based compound can be prepared with high purity and high yield, by easily introducing an acrylic structure into highly sterically hindered alcohol using a diamine-based compound and acid anhydride.

DETAILED DESCRIPTION OF THE EMBODIMENTS

Hereinafter, preferable examples are presented for better understanding of the invention. However, these examples are presented only as the illustrations of the invention, and the scope of the invention is not limited thereby.

Example 1

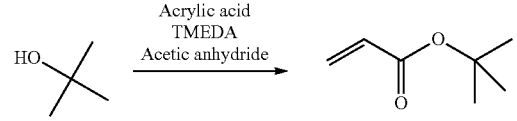

Into a 100 ml flask, 2.3 g (30 mmol) of t-BuOH and 4.3 g (60 mmol) of acrylic acid were introduced, and slowly stirred in an ice bath of 0° C. or less. Into the flask, 3.5 g (30 mmol) of N,N,N',N'-tetramethylethylenediamine (TMEDA) was slowly introduced while taking care about exotherm. After completing the introduction, the flask was transferred to a 60° C. oil bath, and 3.8 g (37.5 mmol) of acetic anhydride was slowly introduced over about 2 hours. After completing the introduction, they were additionally stirred at 60° C. for 3 hours, and conversion was confirmed through TLC and GC. After confirming the termination of the reaction, hexane was introduced into the resulting reactant, and the mixture was stirred to extract. The hexane layer at the upper part of the extract was separated, and the organic salt layer at the lower part was extracted once again using hexane. The collected hexane layer was washed once with water. The residual moisture in the hexane layer was removed with MgSO$_4$, and then, hexane was removed through vacuum distillation, thus obtaining acrylic acid ester of the above structure (yield: 66%, conversion: >99%, purity: >95%).

1H NMR (CDCl$_3$, 500 MHz): 6.30 (m, 1H), 6.07 (m, 1H), 5.72 (m, 1H), 1.52 (s, 9H)

Example 2

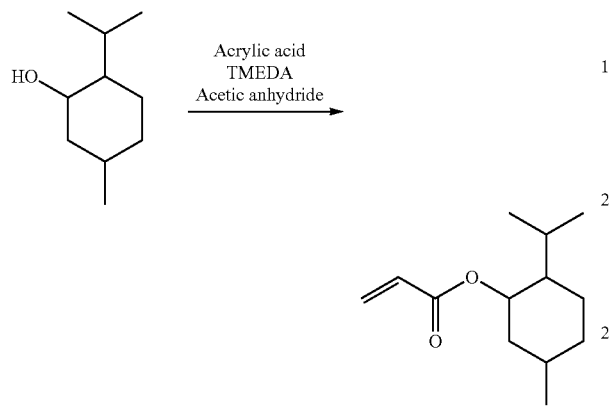

Into a 100 ml flask, 4.7 g (30 mmol) of menthol and 4.3 g (60 mmol) of acrylic acid were introduced, and slowly stirred in an ice bath of 0° C. or less. Into the flask, 3.5 g (30 mmol) of TMEDA was slowly introduced while taking care about exotherm. After completing the introduction, the flask was transferred to a 60° C. oil bath, and 3.8 g (37.5 mmol) of acetic anhydride was slowly introduced over about 2 hours. After completing the introduction, they were additionally stirred at 60° C. for 3 hours, and conversion was confirmed through TLC and GC. After confirming the termination of the reaction, hexane was introduced into the resulting reactant, and the mixture was stirred to extract. The hexane layer at the upper part of the extract was separated, and the organic salt layer at the lower part was extracted once again using hexane. The collected hexane layer was washed once with water. The residual moisture in the hexane layer was removed with MgSO$_4$, and then, hexane was removed through vacuum distillation, thus obtaining acrylic acid ester of the above structure (yield: 86%, conversion: >99%, purity: >95%).

1H NMR (CDCl$_3$, 500 MHz): 6.39 (dd, J=17.4 Hz, 1.2 Hz, 1H), 6.10 (dd, J=17.4 Hz, 10.5 Hz, 1H), 5.79 (dd, J=10.5 Hz, 1.2 Hz, 1H), 4.76 (dt, J=11.0 Hz, 4.6 Hz, 1H), 2.11 (m, 1H), 1.87 (m, 1H), 1.68 (m, 1H), 1.50 (m, 1H), 1.41 (m, 1H), 1.11-0.95 (m, 2H), 0.90 (dd, J=7.9 Hz, 6.8 Hz, 6H), 0.76 (d, J=7.1 Hz, 3H)

Comparative Example 1

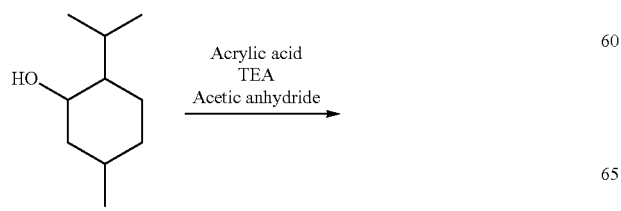

Acrylic acid ester of the above structure was obtained by the same method as Example 2, except that triethylamine (TEA) was used instead of TMEDA (yield: 66%, conversion: >99%, purity: >60%). It was confirmed that acetylated by-products were produced about 30%, as the result of the reaction.

Comparative Example 2

Into a 100 ml flask, 2.3 g (30 mmol) of t-BuOH, 4.2 g (33 mmol) of acrylic anhydride, and 200 ppm of polymerization inhibitor MEHQ (4-methoxyphenol) were introduced, and stirred at 60° C. for 10 hours, and conversion was confirmed through TLC and GC. After termination of the reaction, hexane was introduced into the resulting reactant, and the mixture was stirred to extract. The hexane layer at the upper part of the extract was separated, and the organic salt layer at the lower part was extracted once again using hexane. The collected hexane layer was washed once with water. The residual moisture in the hexane layer was removed with MgSO$_4$, and then, hexane was removed through vacuum distillation, thus obtaining acrylic acid ester of the same structure as Example 1 (conversion: <5%).

The invention claimed is:
1. A method for preparing a (meth)acrylic acid ester-based compound of the following Chemical Formula 1, comprising reacting an alcohol-based compound of the following Chemical Formula 2 and a (meth)acrylic acid-based compound of the following Chemical Formula 3, in the presence of a diamine-based compound of the following Chemical Formula 4 and an acid anhydride of the following Chemical Formula 5:

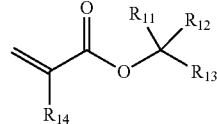

[Chemical Formula 1]

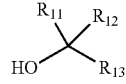

[Chemical Formula 2]

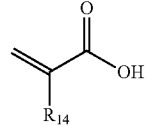

[Chemical Formula 3]

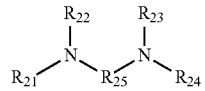

[Chemical Formula 4]

[Chemical Formula 5]

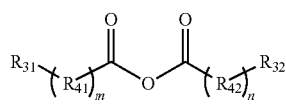

wherein in the Chemical Formulae 1 to 5, $R_{11}$ to $R_{13}$ are each independently, hydrogen, substituted or unsubstituted $C_{1-20}$ alkyl, or substituted or unsubstituted $C_{3-20}$ cycloalkyl, or two neighboring functional groups are linked to form an alicyclic structure, $R_{14}$ is hydrogen or methyl, $R_{21}$ to $R_{24}$ are each independently, hydrogen, or substituted or unsubstituted $C_{1-10}$ alkyl, $R_{25}$ is substituted or unsubstituted $C_{1-10}$ alkylene, $R_{31}$ and $R_{32}$ are each independently, hydrogen or methyl, $R_{41}$ and $R_{42}$ are each independently, substituted or unsubstituted $C_{1-10}$ alkylene, m and n are each independently, an integer of 0 or 1, provided that when both m and n are 0, each of $R_{31}$ and $R_{32}$ is methyl.

2. The method according to claim 1, wherein $R_{11}$ to $R_{13}$ are each independently, hydrogen, substituted or unsubstituted $C_{1-20}$ alkyl, or substituted or unsubstituted $C_{3-20}$ cycloalkyl, or two neighboring functional groups are linked to form an alicyclic structure, provided that two or more of $R_{11}$ to $R_{13}$ are not simultaneously hydrogen.

3. The method according to claim 1, wherein the alcohol-based compound is a compound of the Chemical Formula 2 in which $R_{11}$ to $R_{13}$ are each independently $C_{1-6}$ linear or branched alkyl, or $C_{3-6}$ cycloalkyl; or a compound of the Chemical Formula 2 in which $R_{11}$ is hydrogen, and $R_{12}$ and $R_{13}$ are linked with each other to form a $C_{6-10}$ alicyclic structure unsubstituted or substituted with $C_{1-6}$ alkyl.

4. The method according to claim 1, wherein the alcohol-based compound is butanol or menthol.

5. The method according to claim 1, wherein the (meth)acrylic acid-based compound is acrylic acid.

6. The method according to claim 1, wherein the (meth)acrylic acid-based compound is used at a mole ratio of 1 to 3, based on 1 mole of the alcohol-based compound.

7. The method according to claim 1, wherein the diamine-based compound is a compound of the Chemical Formula 4, in which $R_{21}$ to $R_{24}$ are each independently, hydrogen; or $C_{1-10}$ alkyl unsubstituted or substituted with $C_{1-6}$ alkyl or $C_{3-6}$ cycloalkyl; and, $R_{25}$ is $C_{1-10}$ alkylene unsubstituted or substituted with $C_{1-6}$ alkyl or $C_{3-6}$ cycloalkyl.

8. The method according to claim 1, wherein the diamine-based compound is N,N,N',N'-tetramethylethylenediamine, N,N-dimethylethylene-1,2-diamine, N,N,N',N'-tetramethylpropylenediamine, or N,N,N',N'-tetramethylbutylenediamine.

9. The method according to claim 1, wherein the diamine-based compound is used at a mole ratio of 0.5 to 1.5, based on 1 mole of the alcohol-based compound.

10. The method according to claim 1, wherein the acid anhydride is a compound of the Chemical Formula 5, in which $R_{31}$ and $R_{32}$ are each independently, hydrogen or methyl, $R_{41}$ and $R_{42}$ are each independently, substituted or unsubstituted $C_{1-6}$ alkylene, and m and n are each independently, an integer of 0 or 1, provided that when both m and n are 0, each of $R_{31}$ and $R_{32}$ is methyl.

11. The method according to claim 1, wherein the acid anhydride is acetic anhydride.

12. The method according to claim 1, wherein the acid anhydride is used at a mole ratio of 1 to 1.5, based on 1 mole of the alcohol-based compound.

13. The method according to claim 1, wherein:
(i) the alcohol-based compound and the (meth)acrylic acid-based compound are first combined to form a mixture;
(ii) the mixture is then mixed with the diamine-based compound, and reacted to form a reactant; and
(iii) the reactant is mixed with the acid anhydride, and reacted,
(i) and (ii) are conducted at a temperature of 0° C. or less, and
the (iii) is conducted at 50 to 80° C.

14. The method according to claim 13, wherein the reactant obtained as the result of the (ii) comprises acryldiaminoalkane cation.

15. The method according to claim 1, further comprising an extraction purification process with hexane, after the reaction.

* * * * *